United States Patent
Halter et al.

(10) Patent No.: US 9,542,481 B2
(45) Date of Patent: Jan. 10, 2017

(54) RADIOLOGY DATA PROCESSING AND STANDARDIZATION TECHNIQUES

(71) Applicant: Virtual Radiologic Corporation, Minneapolis, MN (US)

(72) Inventors: Jordan Halter, Minneapolis, MN (US); Justin Richie, Minneapolis, MN (US); Allan Swenson, Minneapolis, MN (US); Kim Gerdeman, Eden Prairie, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 323 days.

(21) Appl. No.: 14/309,503

(22) Filed: Jun. 19, 2014

(65) Prior Publication Data
US 2014/0379718 A1 Dec. 25, 2014

Related U.S. Application Data

(60) Provisional application No. 61/838,038, filed on Jun. 21, 2013.

(51) Int. Cl.
*G06F 17/30* (2006.01)
*G06F 19/00* (2011.01)

(52) U.S. Cl.
CPC ....... *G06F 17/30705* (2013.01); *G06F 19/321* (2013.01)

(58) Field of Classification Search
None
See application file for complete search history.

(56) References Cited

U.S. PATENT DOCUMENTS

2008/0004505 A1 1/2008 Kapit et al.
2009/0083285 A1* 3/2009 Krause ................ G06F 12/0802

(Continued)

OTHER PUBLICATIONS

"CMS Manual System Pub 100-04 Medicare Claims Processing", [online]. Retrieved from the Internet: <URL: http://www.cms.gov/Regulations-and-Guidance/Guidance/Transmittals/downloads/R2141CP.pdf>, (Jan. 24, 2011), 55 pgs.

(Continued)

*Primary Examiner* — Richard Bowen
(74) *Attorney, Agent, or Firm* — Schwegman Lundberg & Woessner, P.A.

(57) ABSTRACT

Systems and methods for establishing standardization of radiology imaging procedure types and data related to such radiology imaging procedure types are disclosed herein. Radiology imaging data produced from radiology procedures at plurality of different systems and locations may produce different data formats and data values, even for the same radiology procedure. In one example, a radiology imaging order system is configured to standardize these different data formats and data values to a standardized format and identification that can be used for radiology study assignment, categorization, analytics, and related data federation activities. In further examples, multiple radiology procedures from respective facilities are normalized to a radiology procedure type schema, with each normalized radiology procedure type identifiable with a human-readable procedure identifier. Other examples of processing activities and use of the procedure identifier and standardized data are also disclosed herein.

28 Claims, 9 Drawing Sheets

(56) References Cited

U.S. PATENT DOCUMENTS

| | | | | |
|---|---|---|---|---|
| 2009/0281836 A1* | 11/2009 | Velarde | ................ | G06F 19/323 |
| | | | | 705/3 |
| 2010/0228721 A1* | 9/2010 | Mok | .................... | G06F 19/322 |
| | | | | 707/711 |
| 2010/0306218 A1 | 12/2010 | Bacon | | |
| 2011/0015941 A1* | 1/2011 | Backhaus | ............. | G06F 19/321 |
| | | | | 705/2 |
| 2011/0119088 A1* | 5/2011 | Gunn | .................... | G06F 19/322 |
| | | | | 705/3 |
| 2011/0197119 A1* | 8/2011 | Ye | .......................... | G06Q 50/22 |
| | | | | 715/226 |
| 2012/0215799 A1* | 8/2012 | Bohner | ................ | G06F 19/322 |
| | | | | 707/755 |
| 2012/0323593 A1 | 12/2012 | Backhaus | | |
| 2014/0016852 A1* | 1/2014 | Soboleski | .............. | A61B 6/502 |
| | | | | 382/132 |
| 2014/0149407 A1 | 5/2014 | Qian et al. | | |

OTHER PUBLICATIONS

International Application Serial No. PCT/US2014/043241, International Search Report mailed Nov. 14, 2014, 2 pgs.
International Application Serial No. PCT/US2014/043241, Written Opinion mailed Nov. 14, 2014, 8 pgs.

* cited by examiner

RADIOLOGY DATA PROCESSING AND STANDARDIZATION TECHNIQUES

RELATED MATTERS

This application claims the benefit of priority to U.S. Provisional Patent Application Ser. No. 61/838,038, filed Jun. 21, 2013, which is incorporated herein by reference in its entirety.

TECHNICAL FIELD

Embodiments pertain to techniques and systems for processing electronic imaging data obtained from medical imaging procedures. Some embodiments relate to data processing mechanisms for electronic radiology imaging data that perform coordination, normalization, and standardization of radiological imaging data.

DETAILED DESCRIPTION

Figure 1:
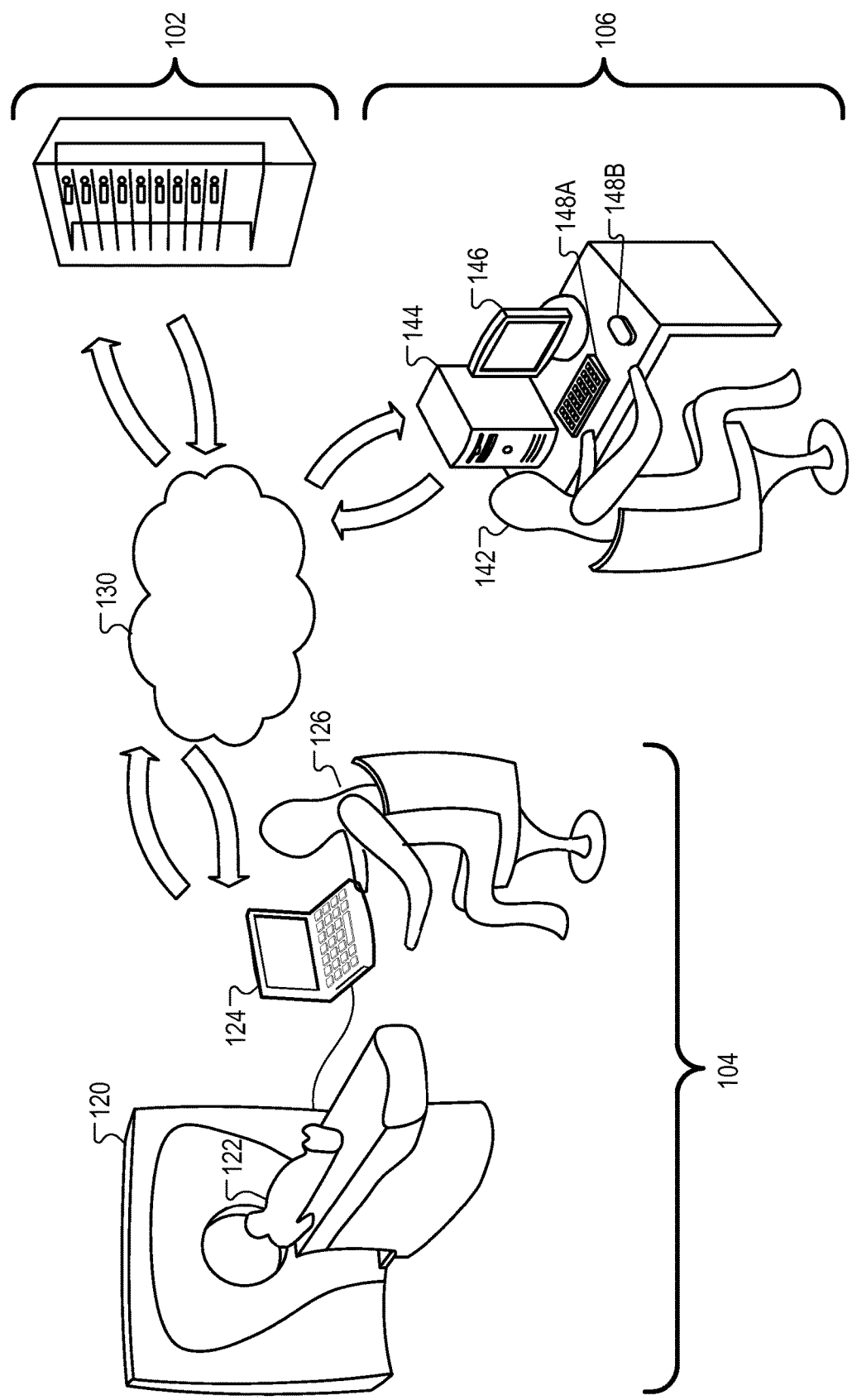
FIG. 1 illustrates a radiology system configuration enabled for processing radiology imaging data and assigning medical imaging requests to remote systems according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations that enable medical imaging studies to be classified and standardized into useful categorizations. Categorizations may be assigned or otherwise designated for specific types of medical imaging procedures (e.g., radiological imaging procedures). For example, a categorization may be designated for a CT imaging of a patient's abdomen body region performed with contrast, where the imaging correlates to a specific medical facility identifier and billing code. In some examples, the categorizations may be provided using data normalization and standardization of various imaging procedure types as identified by medical facilities and in the imaging data. In other examples, the categorizations may be provided using additional data fields and attributes applied to the imaging data (and other electronic information associated with the imaging procedure).

Medical imaging data obtained from medical imaging procedures at respective medical facilities often provides raw, unorganized facts needing contextual processing. Even if accompanied by some basic identifiers, this medical imaging data may be random or not useful with other types of data (especially in large quantities) until it is organized. As a common example, different medical facilities and medical systems often use different names, identifiers, and codes for the same underlying radiological imaging procedures. The techniques described herein enable medical imaging data produced from various types of imaging procedures at different medical facilities and medical systems to be organized, structured, processed, and presented in a consistent context.

The categorization and standardization of data from radiological imaging procedures at different locations enables radiology processing systems to quickly determine relevant data values that are relevant to a some goal (such as increasing assignment accuracy, reducing turn-around-times, and the like). The categorization and standardization of data also makes the data obtained from the respective radiological imaging procedures to be useful and actionable for evaluation in large-scale processing setting.

The categorization and standardization of data from disparate radiology imaging procedures types also may assist with a variety of forms of radiology analytics (e.g., informatics). (While the term "analytics" may be used to refer to low-level analysis and reporting, and while the term "informatics" may be used to refer to higher-level statistical analysis, the two terms are here used interchangeably to refer to similar analysis and reporting operations.) Radiology analytics intends to improve the efficiency, accuracy, usability, and reliability of medical imaging services within a healthcare enterprise. Informatics provides study and application of how information about, accompanying, and contained within radiology studies are retrieved, analyzed, enhanced, and exchanged throughout the medical enterprise. For example, for teleradiology operations, useful information can be correlated to radiology imaging procedure types. This useful information may be produced from a variety of data processing operations involving medical facilities, local radiologists and radiology practices, a teleradiology provider, and remote radiologists and radiology practices. In addition, informatics may apply Natural Language Processing in connection with various analytic techniques to improve performance and accuracy of the processing operations.

In many of the following examples, disparate radiology procedure types are performed at a variety of imaging modalities (e.g., computed tomography (CT), magnetic resonance imaging (MRI), Ultrasound, etc.), medical facilities, and geographic locations. The data types produced from the various types of procedures are processed to normalize known procedures into a consolidated list of procedures. This consolidated list of procedures may be defined to correlate to expanded data characteristics, such as CPT (Current Procedural Terminology) Codes, CMS (Centers for Medicare & Medicaid) RVU (Relative Value Unit) Values, and the like. With data standardization, stored data fields may become relational, which gives further leveraging into the use of business analysis and informatics from standardized data. In addition, the standardization on these data fields may enable known data types to become fixed or "locked down", to enable more accurate and consistent data type usage.

FIG. 1 provides an illustration of an example radiology system configuration 100 enabling the processing of radiology medical imaging procedures according to an example described herein. The radiology system configuration 100 may be used for capturing medical image data in one location and for reviewing medical images associated with the data in another location. The radiology system configuration 100 may include many geographically separated imaging devices and many image review terminals. The radiology system configuration 100 may operate as a remote teleradiology system connected to a plurality of healthcare locations, as a localized radiology system used in a single hospital, healthcare provider network, or private radiology practice. The radiology system configuration 100 may also operate as an information processing network used to process data from respective radiology procedures regardless of the location of an eventual radiological study read.

For purposes of illustration, the radiology system configuration 100 depicted in FIG. 1 includes an imaging system 104, a radiology imaging order processing system 102, and an image review system 106. The imaging system 104, for example, may include an imaging device 120, such as a CT scanner, a MRI scanner, or another imaging system (e.g., a radiology imaging modality). Using an energy source such as x-rays or magnetic fields, for example, the imaging device 120 may capture image data associated with a subject 122 (e.g., a patient).

The imaging device 120 may be controlled by a radiology technician 126 at the medical facility through the use of a workstation terminal or other electronic input control 124. Prior to the radiology technician 126 conducting the imaging procedure for a patient, information may be entered into the electronic input control 124. Information from an electronic medical record (EMR) or healthcare information system (HIS) may also be accessed for the imaging procedure. Relevant information and metadata for the radiology imaging procedure may be placed within the radiological image itself, or within another data store for further access and processing. For example, the imaging device 120 may produce radiological images generally consistent with the Digital Imaging and Communications in Medicine (DICOM) format, other industry-accepted standards, or proprietary standards.

Consistent with the appropriate image format, the images produced by the image data source may include metadata. This metadata may be generated by the imaging device 120, from input collected by the electronic input control 124, or from input from a HIS. Further, the series of images may be obtained directly by the imaging device 120 in the facility shown in FIG. 1, or may be transferred in whole or in part from another image capturing device connected to the imaging device 120 or the medical facility's local network. The imaging data source may also include data transmitted through use of a local facility imaging server (not shown), such as a DICOM server or other Picture Archiving and Communication System (PACS).

The metadata within each imaging data file may include identification information such as patient identifier and an identifier of the series of images, in addition to information about the type of imaging modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images. In some implementations, the image data may be used to produce a three-dimensional model that can be further manipulated and reformatted for generating two-dimensional (or three-dimensional) images. Image data captured by the imaging device 120 may be stored and processed by the radiology imaging order processing system 102 or another local or remote imaging device server (e.g., one or more computers with a processor and a memory), and may be provided to other systems and computers in the radiology system configuration 100 through network 130 (e.g., an intranet or the Internet).

In some implementations, image data provided to the radiology imaging order processing system 102 results in data being stored and processed by one or more computers. For example, the radiology imaging order processing system 102 may determine that the image data is to be forwarded to a viewing system user 142 (e.g., a radiologist) at an image review system 106. As shown, image data may be provided by the radiology imaging order processing system 102 through the network 130 to the image review system 106.

The image review system 106, for example, may include an image display server 144 (e.g., one or more computers with a processor and a memory), a display device 146 (e.g., a monitor), and input devices 148A-148B (e.g., keyboards, computer mice, joysticks, touch interfaces, voice recognition interfaces, and the like). In some implementations, image data may be processed by the image display server 144 and visually presented to the user 142 as one or more images at the display device 146. Using the input devices 148A-148B, the user 142 may interact with the presented images, for example, by manipulating one or more user controls included in a graphical user interface presented at the display device 146 in association with the images. For example, the user 142 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the user 142 may indicate a diagnostic finding or produce a diagnostic finding output related to a radiological imaging procedure performed on the subject 122.

When the radiology imaging order processing system 102 receives the image, it may process the image with an image server. This processing may include compressing or converting the image to a different format using a compressor/converter module. This image server may also operate to extract metadata from each image file in a series of radiology scan images. For example, the extracted metadata may include header data for the image providing patient information and hospital information for the hospital that sent the image. The image server may then store all or part of the extracted information in a study record that may be correlated with appropriate orders and studies. The radiology imaging order processing system 102 may operate to process related radiology orders or correlate a radiology order with study images.

In some examples, the lateral and horizontal movement of studies between an onsite facility and any remote/cloud location uses a closely orchestrated feed utilizing HL7 (Health Level 7) and DICOM standards. The data produced from HL7 and DICOM communications for radiology studies and like medical diagnostic imaging procedures provides a useful application of data in need of standardization.

In medical operational environments, messages containing data about patients are sent across the hospital network from one system to another. This data contains information about patient demographic, the diagnostic encounter, charges, and the like. The data may be formatted in a common standard used across healthcare organizations, such as using standards defined according to the HL7 specification as developed by the HL7 organization. HL7 is an interface protocol at the application level designed for communications among healthcare applications and systems. HL7 standard formats are used for sending messages to enable the destination information systems to understand the data presented.

HL7 includes a definition for several types of messages. In the radiology processing setting, three message types often used are the ADT, ORM, and ORU message types (as these message types create the most pathways in the interfaces). The ADT message, or "Admit Discharge Transfer," is sent when a patient's registration status in the hospital changes. Within the ADT message, "Admit" represents when a patient enters the hospital or other medical facility, "Discharge" represents when the patient leaves the hospital or facility, and "Transfer" represents when the patient moves to a different unit or to a different hospital or facility. The ADT message alerts medical information systems to expect a patient and to expect possible further transmissions of messages. Information systems receive this ADT message if they interact with the patient's data. The ORM, or "Order Message," is sent when a healthcare provider requests a service, procedure, or treatment for a patient. Any information system involved to fulfill this order needs to receive this message. The ORU message, or "Observational Report—Unsolicited," is typically returned in response to the ORM message and contains the results from the request. For example, the ORU message may be used to transmit the results from a test or image.

HL7 provides a standardized format for these and other messages, but the data fields that are populated within the respective messages can vary significantly. Accordingly, this makes communication between different sites and communication processing from such different sites extremely difficult. The following sections describe standardization and categorization techniques used to adapt common applications despite the different data formats and content of HL7 messages and similar communications in connection with medical diagnostic imaging procedures. Such standardization and categorization may be used to establish accurate connections of data fields to the respective medical facilities connected to the radiology imaging order processing system 102.

In one example, a standardized data representation is established for respective medical imaging procedure types (e.g., radiology procedure types) based on a plurality of data fields. These data fields may include a combination of industry standard characteristics tied to the radiology procedure (such as a CPT Code), localized processing fields relevant to the radiology processing provider (such as data values used by a teleradiology provider), and standardization information, such as a unique key or other standardized identifier for the particular "type" of imaging procedure.

With the orchestration of common data fields for differing radiology imaging procedures, various identifiers and data value representations received from various medical facilities can be correlated and referenced to a common data set. Further, the standardization information enables data fields to be locked down and controlled, so data fields used with downstream processing can be more accurate and consistent.

The standardization of a list of radiology procedures may correlate to the use of a unified radiology procedure identifier or key, further referred to as a "vCode." The vCode may serve in an image processing system as an unique procedure code that facilitates a translation of a common procedure type between multiple radiology processing systems (such as multiple sources which each provide data for a common procedure type in a slightly different fashion). With use of the vCode, nomenclature can be defined to help translate how diagnostic imaging reads are moved between local and remote sources, and from the "grid" of local facilities and radiologists to the "cloud" where many remote radiologists can operate.

The vCode may also be used to facilitate logic for additional processing activity. For example, logic may be defined that can route certain types of radiology reads more accurately to respective radiologists based on the radiologists' location and subspecialty. The vCode may also be used to tie radiology procedures to specific location and subspecialty attributes that would not otherwise be immediately determinable from an identifier provided in an HL7 message or DICOM medical imaging data. In addition, the vCode may also be used to facilitate logic that has embedded restrictions, to optimize performance, scheduling, and analysis of imaging procedures and associated diagnostic activities.

The standardization of data to the vCode may be enabled through a definition of what procedures and information will be provided from a "clean" data feed. For example, the integration of hundreds or thousands of medical facilities and each facility's respective procedures into a system, would lead to an exponential rise in procedures and procedure rules that a radiology imaging order processing would need to track and maintain. The creation of a unique procedure code for each procedure as performed at each respective medical facility leads to many inefficiencies, and turns radiological study assignment from being an automated process into an exceptions-based engine. The standardization of data to the vCode therefore may serve as not only a mechanism of normalizing disparate data fields, but also operate to reduce inefficiencies, identify inactive procedures, and consolidate outdated CPT codes, outdated RVUs, and ambiguous descriptions. Further, the use of the vCode also enables the conversion of radiological procedure data into a relational format, which enables in depth analysis into operations conducted in a radiology evaluation workflow.

Figure 2:
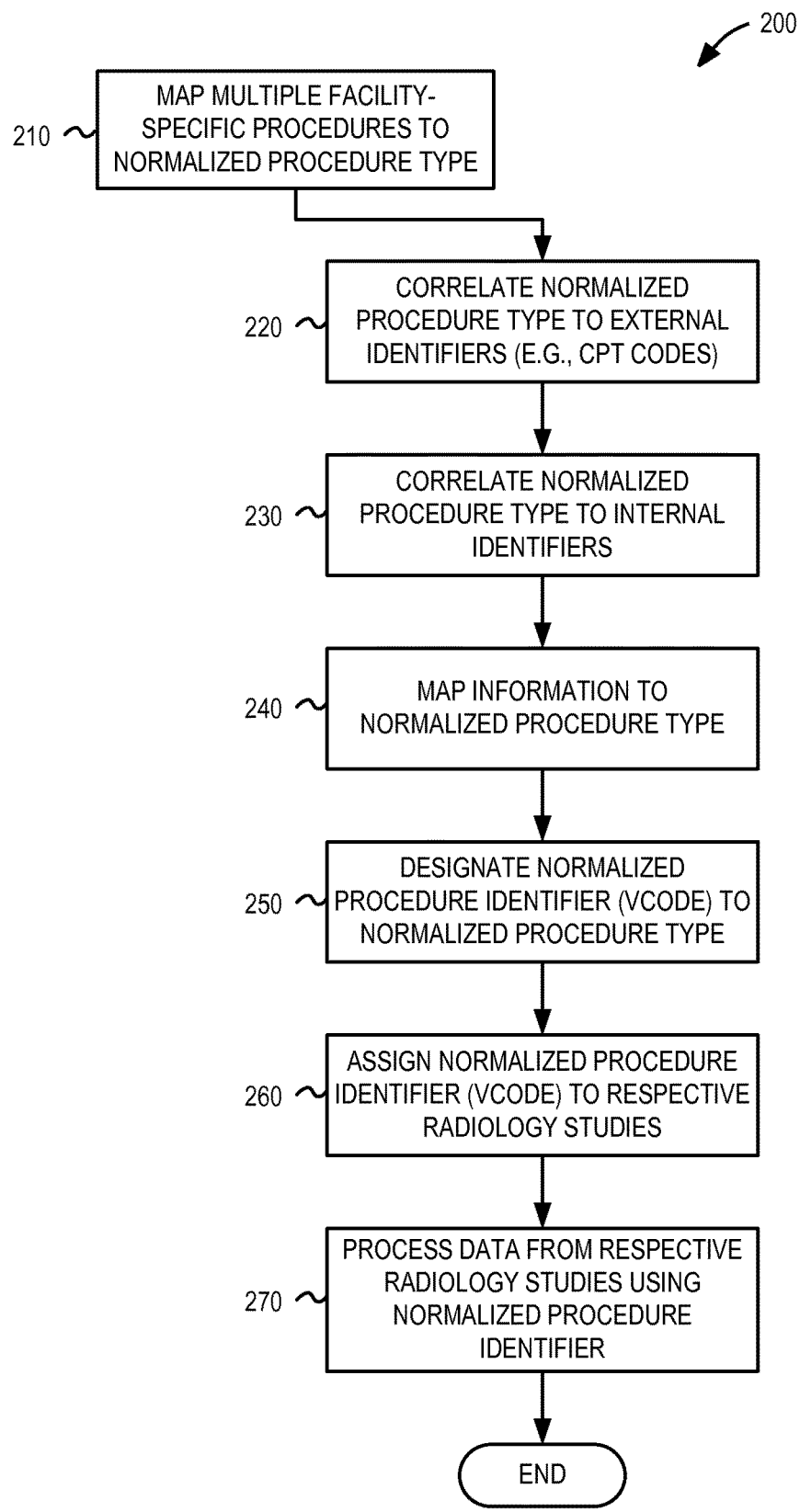
FIG. 2 illustrates a flowchart of a technique for normalizing and standardizing radiology imaging procedure types according to an example described herein.

FIG. 2 provides a flowchart 200 of a data standardization process that may be performed in a radiology processing system, such as the radiology imaging order processing system 102, according to an example described herein. This data standardization process may be initiated through the mapping of various facility-specific procedures (which would otherwise be identified as multiple procedure types) to a normalized procedure type (operation 210). For example, this mapping may occur by a medical service provider performing a mapping of "different"-appearing procedures of a specific anatomy, produced at respective medical facilities, to a common procedure type such as a "Spine MRI". As discussed below, this normalized procedure type is established to become associated with attributes that are correlated with common characteristics of the procedure type (and the underlying procedure(s)) that are present among the various medical facilities.

The specific mapping operations may include the correlation of a normalized procedure type to one or more external identifiers (operation 220). For example, multiple CPT codes that are used by various medical facilities (e.g., for a Spine MRI) can be correlated to a particular normalized procedure type. Next, the normalized procedure type may be correlated to one or more internal identifiers (operation 230). For example, a teleradiology provider may utilize various internal identifiers to track the various permutations of procedure types at respective facilities, medical facility groups, and the like.

The determined relevant information, including the external identifiers and the internal identifiers, is then mapped to a normalized procedure type (operation 240). This mapping may include the use of a database table, relational database structure, or other data structure to create and persist a relationship between the data values. In this relationship, a normalized procedure identifier (e.g., the vCode described herein) may be designated to serve as a unique identifier of the normalized procedure type (operation 250). In similar examples, a standardized procedure identifier may be designated to serve as an identifier of the procedure type (for example, for scenarios where the identifier is not necessarily unique or fully normalized for all procedure types).

Once the data standardization to a normalized procedure type is established, respective medical imaging procedures (e.g., radiology studies) can be assigned or correlated to the normalized procedure identifier (or standardized procedure identifier) associated with the normalized radiology procedure type (operation 260). Accordingly, data from respective medical imaging procedures (e.g., radiology studies) for the procedure type can be processed, routed, and directed using the normalized procedure identifier (operation 270).

Figure 3:
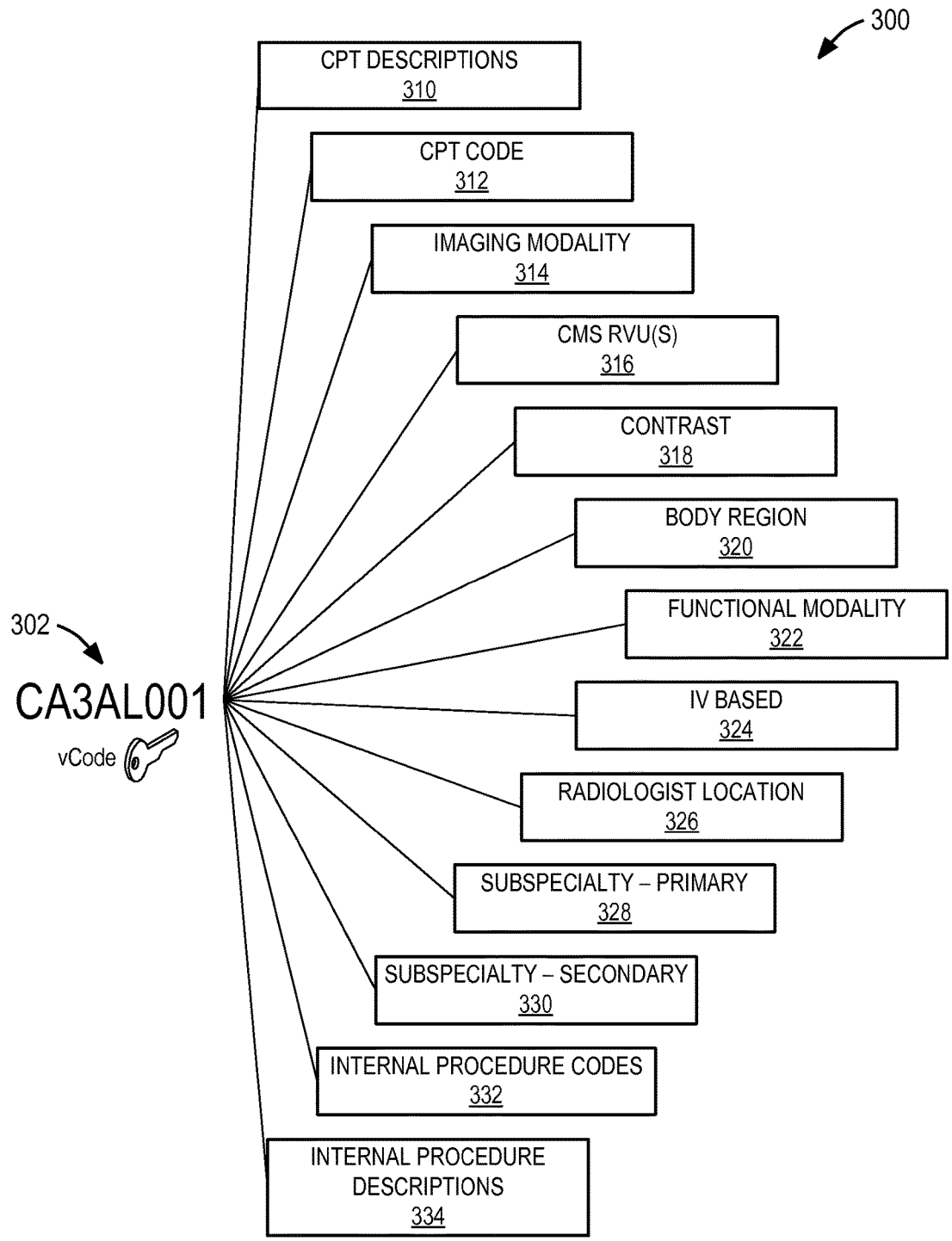
FIG. 3 illustrates a standardized data definition for an example normalized procedure identifier according to an example described herein.

FIG. 3 illustrates a standardized data definition and association 300 for a normalized procedure identifier of a radiology procedure type according to an example described herein. In a diagnostic radiology imaging setting, these data types may include fields relevant to imaging studies and the particular imaging processor (e.g., a radiology or teleradiology practice which conducts reads of the imaging studies).

In the detailed data definition and association provided for example vCode 302 depicted in FIG. 3, the various definitions associated with the vCode 302 for the normalized procedure include: CPT Description 310, CPT Code 312, Imaging Modality 314, CMS Total RVU(s) 316 (e.g., Technical RVU, Professional RVU, Total RVU, or Work RVU), Contrast 318, Body Region 320, Functional Modality 322, IV Based 324, Radiologist Location 326, Subspecialty-Primary 328, Subspecialty-Secondary 330, Internal Procedure Codes 332, or Internal Procedure Descriptions 334. The combination of these definitions may be used to establish a normalized procedure identifier that can serve as an internal, industry, or third party identifier. Accordingly, the vCode 302 serves as an identifier or key that can be associated with the data field definitions 310-334. As further illustrated in FIG. 4, some of these data field definitions associated to or correlated with the vCode 302 may contribute to the values and format of the vCode 302 itself.

In a basic data management example, a standardized data definition may be structured with a simple data table format, such as in a table containing rows with data for respective radiology procedure types, and columns that indicate relevant data types that are relevant to standardization. These data characteristics may be associated with data values defined according to an industry standard or unique to the image processing provider (e.g., radiology or teleradiology practice). For example, a table for the standardized data characteristics may map data values in the following configuration:

Column A: CPT Code 312 (Industry Standard)
Column B: vCode Descriptions (Unique)
Column C: CPT Description 310 (Industry Standard)
Column D: Comments (Unique)
Column E: Imaging Modality 314 (Industry Standard)
Column F: CMS Technical RVU (Fiscal) (Industry Standard)
Column G: CMS Professional RVU (Industry Standard)
Column H: CMS Total RVU (Productivity) (Industry Standard)
Column I: CMS Work RVU (Industry Standard)
Column J: vCode 302 (Unique vCode)
Column K: Contrast 318 (Industry Standard)
Column L: Body Region 320 (Industry Standard)
Column M: Modifiers (Industry Standard)
Column N: Functional Modality 322 (Unique)
Column O: Intravenous therapy (IV) Based 324 (Industry Standard)
Column P: Radiologist Location 326 (Unique)
Column Q: Subspecialty-Primary 328 (Unique)
Column R: Subspecialty-Secondary 330 (Unique)
Column S: Prelim Work Units (Unique)
Column T: Final Work Units (Unique)
Column U: Mapped Internal Procedure Codes 332 (Unique)
Column V: Internal Procedure ID (Unique)

In further examples, graphical user interfaces (GUIs) may be built to interface interactions and updates to the standardized data characteristics and standardized procedure definitions. For example, a GUI may be used to interface the standardized data characteristics and standardized procedure definitions with a variety of other systems, to allow for automation for data updates by the image processing provider. For example, when data fields such as CMS RVU Values are updated, a related internal data field such as RVU/WU (RVU work units) may be updated at the same time.

In other examples, the data mappings of specific normalized procedures may be updated as additional medical facility types are recognized; and likewise, additional normalized procedures may be added upon the use of distinct procedures. Although the data may become standardized and can serve as a "locked-down" version of data, the mapping may be updated to additional identifiers on a regular basis by the image processing provider (whether on a schedule, annually, on demand).

Some of the benefits of data standardization to a particular normalized procedure type and a normalized procedure identifier (e.g., the "vCode") include the establishment of consistent mapping despite the usage of different identifiers and data formats for different medical facilities. For example, a vCode may be used to map multiple internal procedure codes (and multiple external procedure codes) to one common procedure type. This may provide particular efficiencies for an image processing provider that handles diagnostic imaging studies from tens or hundreds of different sources.

A normalized procedure identifier may also be used to correlate internal/external procedure codes to additional information attributes useful in a diagnostic imaging practice. For example, a CPT code may indicate a specific procedure but does not indicate what radiology subspecialty is most appropriate to handle the study; a CPT code does not directly indicate a "functionality modality" such as whether a study is an interventional radiology procedure; and a CPT code may not be associated with all relevant work units for preliminary versus final reads. These and other information attributes may be associated and conveyed through the use of the normalized procedure identifiers described herein.

Figure 4:
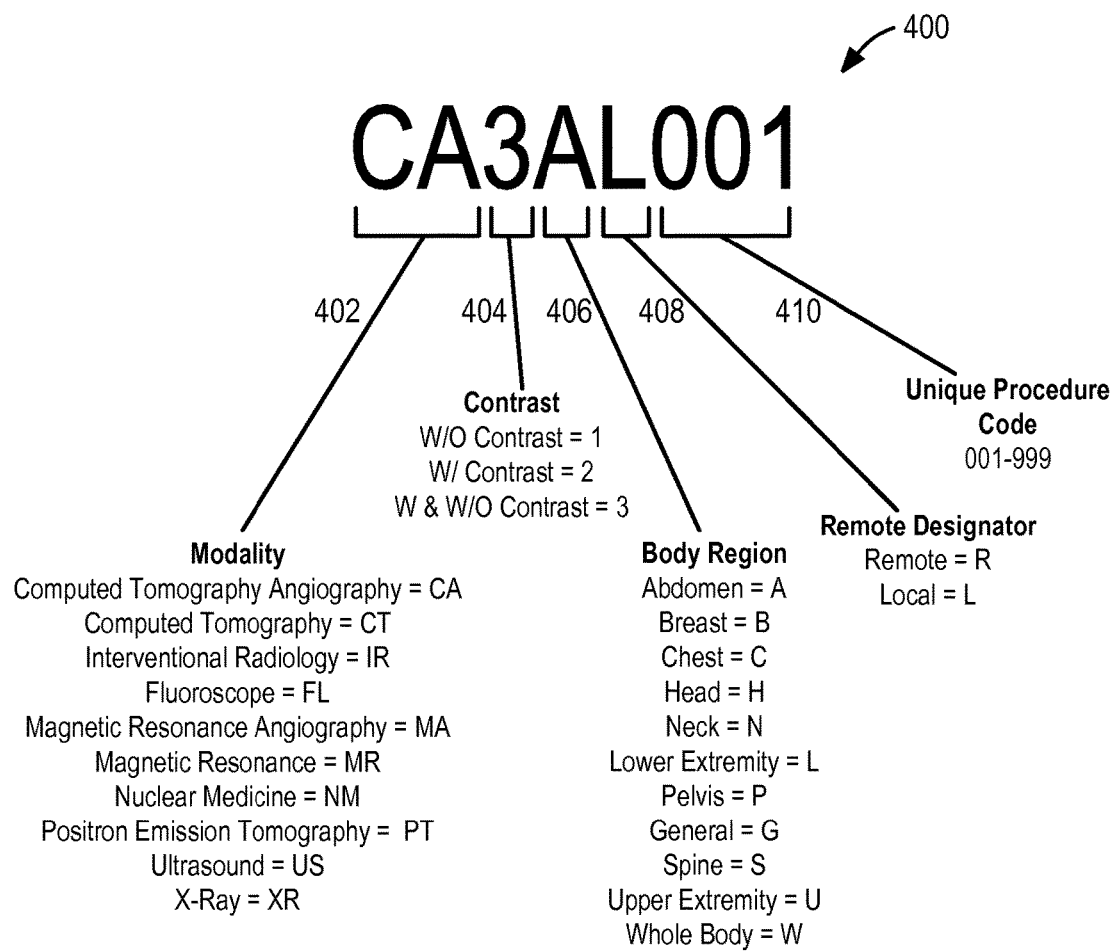
FIG. 4 illustrates a format of an example normalized procedure identifier used in connection with a designation to a radiology imaging procedure type according to an example described herein.

FIG. 4 illustrates a data format and mapping of an example normalized procedure identifier used in connection with a designation to a radiology imaging procedure type according to an example described herein. In one example, the vCode is structured to serve as an identifier of the radiology imaging procedure type that directly indicates characteristics not identified by an external identifier. FIG. 4 provides an illustration of an example vCode 400 including a combination of identifying information components from respective standardized data fields. For example, the vCode 400 is depicted as including components of a unique identifier to indicate values from multiple standardized data fields: Modality, Contrast, Body Region, Remote or Local Designator, and a Unique Procedure Code. Further, the vCode may not only serve as a machine-readable identifier, but may also serve as a human-readable identifier that is easily parseable (and conveys numerous fields of information in a short space).

The vCode 400 may be associated as a unique identifier with a set of data characteristics (e.g., data characteristics depicted in FIG. 3) in a standardized data schema, to allow translation between local and cloud radiology read resources based on the value expressed within the vCode 400. Accordingly, the vCode 400 may operate as a variable that connects and orchestrates the flow of diagnostic imaging reads between local and cloud (remote) facilities. The vCode 400 identifier indicates not only which specific procedure has been performed, but is also associated with a plurality of attributes that provide context and usefulness for actions performed on the underlying data obtained from the procedure.

The vCode 400 thus can be constructed from standardized data values expressing characteristics of a particular medical imaging procedure, with the standardized data values indicating standardized, identifiable characteristics of the type of the particular medical imaging procedure (expressed from among multiple types of medical imaging procedures). An example of the nomenclature for identifier CA3AL001, depicted in vCode 400 of FIG. 4, is as follows:

Modality 402 (indicating value CA, representing Computed Tomography Angiography)

Contrast 404 (indicating value 3, representing with and without Contrast)

Body Region 406 (indicating value A, representing Abdomen)

Remote or Local 408 (indicating value L, representing a locally conducted read)

Unique Procedure 410 (indicating value 001, representing a unique procedure code for the medical diagnostic imaging procedure)

Other unique identifiers and data type indications may be added or substituted within the vCode 400 identifier.

As an explanation of other possible values of the vCode 400 identifier, the Modality portion 402 of the vCode 400 may represent values such as: Computed Tomography Angiography (CA), Computed Tomography (CT), Interventional Radiology (IR), Fluoroscope (FL), Magnetic Resonance Angiography (MA), Magnetic Resonance (MR), Nuclear Medicine (NM), Positron Emission Tomography (PT), Ultrasound (US), or X-Ray (XR). Contrast portion 404 of the vCode 400 may represent values such as: Without Contrast (1), With Contrast (2), or With and Without Contrast (3). Body Region portion 406 of the vCode 400 may represent values such as: Abdomen (A), Breast (B), Chest (C), Head (H), Neck (N), Lower Extremity (L), Pelvis (P), General (G), Spine (S), Upper Extremity (U), or Whole Body (W). Remote Designator portion 408 of the vCode 400 may include Remote (R) or Local (L). Unique Procedure Code portion 410 of the vCode 400 may include an alphanumeric identifier of a particular procedure type, such as a numerical code between 001 and 999. In some examples, the vCode 400 may not include the Remote Designator portion 408 or the Unique Procedure Code portion 410. In other examples, additional data fields such as a specialty or subspecialty portion (not depicted) may be added to the vCode 400. Other variations on the structure and content of the vCode 400 may also be provided based on usage of the identifier in an information system.

Based on the structure of the vCode 400, data operations for the medical diagnostic imaging procedure can apply filtering and selection from one or more of the values (e.g., values 402, 404, 406, 408, 410) defined by the nomenclature. For example, if the vCode indicates "CT," filters can be easily created and applied based on this modality. Remote radiologists who have a modality preference indicated as part of their specialty preference (which is characterized by their primary or secondary subspecialty) may be easily selected using the identifier directly.

The vCode may be used in connection with other aspects of radiology study assignments and processing. For example, a radiologist may have expertise in a body imaging subspecialty, but they are not eligible to read the study, so the study cannot be sent to that radiologist. With the vCode, a simple mechanism and filter may be used to differentiate the procedure type by body region, to ensure that procedures do not arrive at radiologists with built in restrictions.

The vCode may also be used to indicate location-based aspects of the radiology procedure type, through use of the remote designator. Location is another important example to differentiate because with the embedded logic of the vCode, procedures can be mapped to the right radiologist using schedule logic (e.g., for remote radiologists scheduled during certain time periods), where the correct radiologist can be located at the correct time. This further assists the orchestration of movement between local and cloud (remote) radiology read resources.

Figure 5:
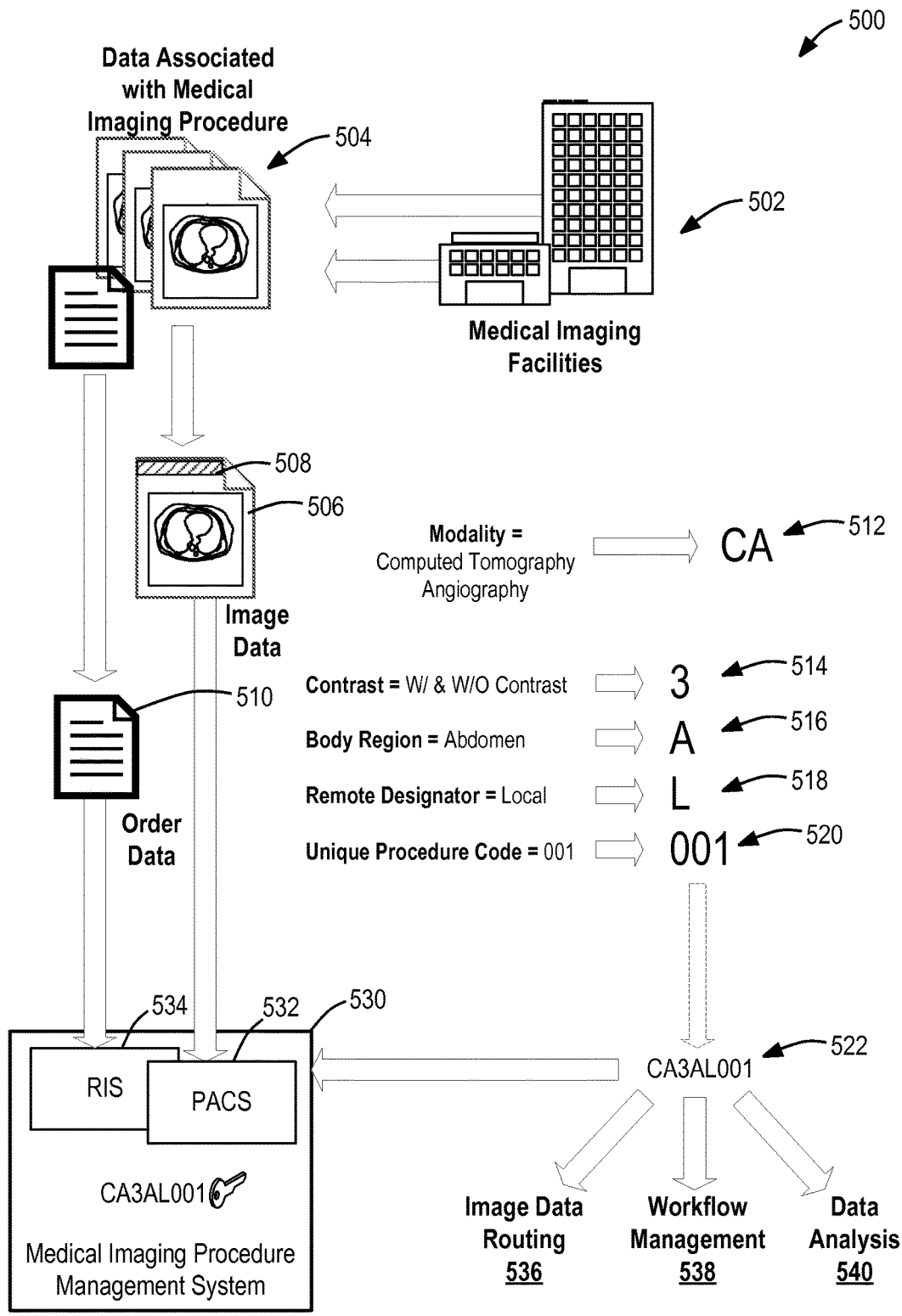
FIG. 5 illustrates system operations in a workflow for generating and routing a set of data produced from a particular radiology study based on a normalized procedure identifier according to an example described herein.

FIG. 5 illustrates a system operations diagram 500 of an example workflow for generating and routing a set of data produced from a particular radiology study based on a normalized procedure identifier 522 according to an example described herein. The data generating and routing system operations diagram 500 is depicted as including image data 506 and order data 510 originating from data of a medical imaging procedure (produced from one or more medical imaging facilities 502). It will be understood, however, that data associated with the medical imaging procedure (e.g., radiology procedure data 504) may also be accompanied or integrated with information from medical information systems (e.g., EMR data, HIS data, and the like) that is not necessarily produced from the medical imaging procedure.

The system operations diagram 500 illustrates a series of operations executable with a radiology processing system, such as the radiology system configuration 100 or specific components of the radiology imaging order processing system 102, for assignment of a normalized procedure identifier or like standardized procedure identifier. These operations include the receipt and processing of the radiology procedure data 504 (e.g., radiology study data, including one or both of a radiology order and a radiology imaging data) from a particular medical imaging facility of the medical imaging facilities 502. This radiology procedure data is processed to obtain identifying data associated with the medical imaging procedure, including an identification of imaging characteristics and type of the radiological procedure. For example, the medical imaging procedure data may include image data 506 or image metadata 508, where the image metadata 508 may include identification information such as patient identifier and an identifier of the series of images, in addition to information about the type of imaging modality and the techniques used to obtain the images. The medical imaging procedure data (e.g., radiology procedure data 504) also may include order data 510, where the order data 510 corresponds to the HL7 Order Message (ORM) sent when a healthcare provider requests a service, procedure, or treatment for a patient.

The image data 506, image metadata 508, and order data 510 may be correlated to generate a normalized procedure identifier (e.g., vCode 522) including a combination of identifying procedure information values, such as example vCode 522. In this example of the nomenclature for identifier CA3AL001, the values are as follows: Modality 512 (indicating CA=Computed Tomography Angiography) (e.g., indicated by image metadata 508), Contrast 514 (indicating W&WO Contrast=3) (e.g., indicated by order data 510), Body Region 516 (indicating Abdomen=A) (e.g., indicated by image metadata 508), Remote Designator 518 (indicating L=Local) (e.g., indicated by order data 510), and Unique Procedure 520 (001) (e.g., indicated by a combination of data from image metadata 508 and order data 510). The individual procedure information values may be combined to form the normalized procedure identifier 522, such as CA3AL001.

In some examples, the values for the vCode 512 may be determined and generated in an automated fashion from an automatic extraction and processing of the image data 506, image metadata, 508 and extractable fields from the order data 510. The values may also be determined by data processing and data values obtained from internal systems (and internal identifiers used in such internal systems), such as a medical image procedure management system 530, a radiology information system (RIS) module 534, or a picture archiving communication system (PACS) module 532). In other examples, rule-based processing and varying levels of human oversight and involvement may be used to direct the creation and assignment of some or all of the fields for the normalized procedure identifier 522.

The normalized procedure identifier 522 may be provided to or assigned within the medical image procedure management system 530 for further use and processing of the image data 508 and the order data 510. For example, the medical image procedure management system 530 may include the PACS module 532, where the PACS module 532 may be used to provide image storage and access features for the image data 506. The medical image procedure management system 530 may further include the RIS module 534, where the RIS module 534 may provide radiology information processing functions for the order data 510. The PACS module 532 and RIS module 534 may use the normalized procedure identifier 522 to organize, correlate, and process the image data 506, image metadata 508, and order data 510. In further examples, the normalized procedure identifier 522 also may be used in connection with the medical imaging procedure management system (or other electronic systems) to perform operations such as image data routing 536, workflow management 538, or data analysis 540.

Figure 6A:
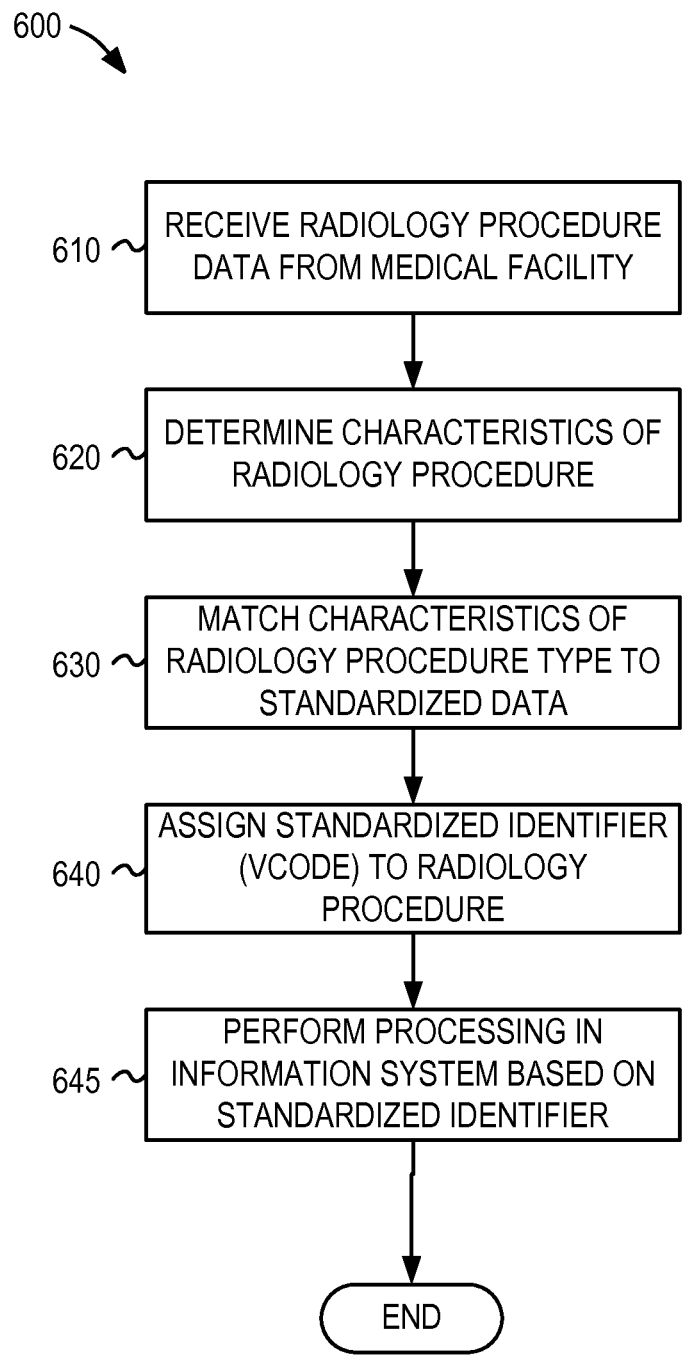
FIG. 6A illustrates a flowchart of an example workflow for processing and standardizing a set of data produced from a particular radiology study according to an example described herein.

FIG. 6A illustrates a flowchart 600 of an example workflow for processing and standardizing a set of data produced from a particular radiology study according to an example described herein. The particular sequence depicted in the flowchart 600 was produced from a particular radiology procedure type, and is provided as a non-limiting example. Accordingly it will be understood that the order of operations may vary depending on the precise data operations to be performed upon the radiology data produced by the radiology imaging procedure.

The flowchart 600 illustrates a series of operations executable with a radiology processing system, such as the radiology system configuration 100 or specific components of the radiology imaging order processing system 102. These operations include the receipt of radiology procedure data from a respective medical facility (operation 610). This radiology procedure data is processed to determine the particular characteristics and type of the radiological procedure (operation 620).

Based on identifying information from the radiology procedure data, the characteristics of the radiology procedure type can be matched to standardized data characteristics and data fields (operation 630). For example, this may involve a match of a CPT code indicated by a HL7 order with a standardized procedure type designated in the radiology processing system. From this match, a standardized identifier may be assigned to the particular radiology procedure conducted in the radiology study (operation 640). This standardized identifier may be a human-readable identifier, such as the vCode described further above. Using the standardized identifier, the radiology study and associated data may be routed, processed, and managed in an information system (operation 645). Further examples of the types of processing operations are further depicted as follows.

Figure 6B:
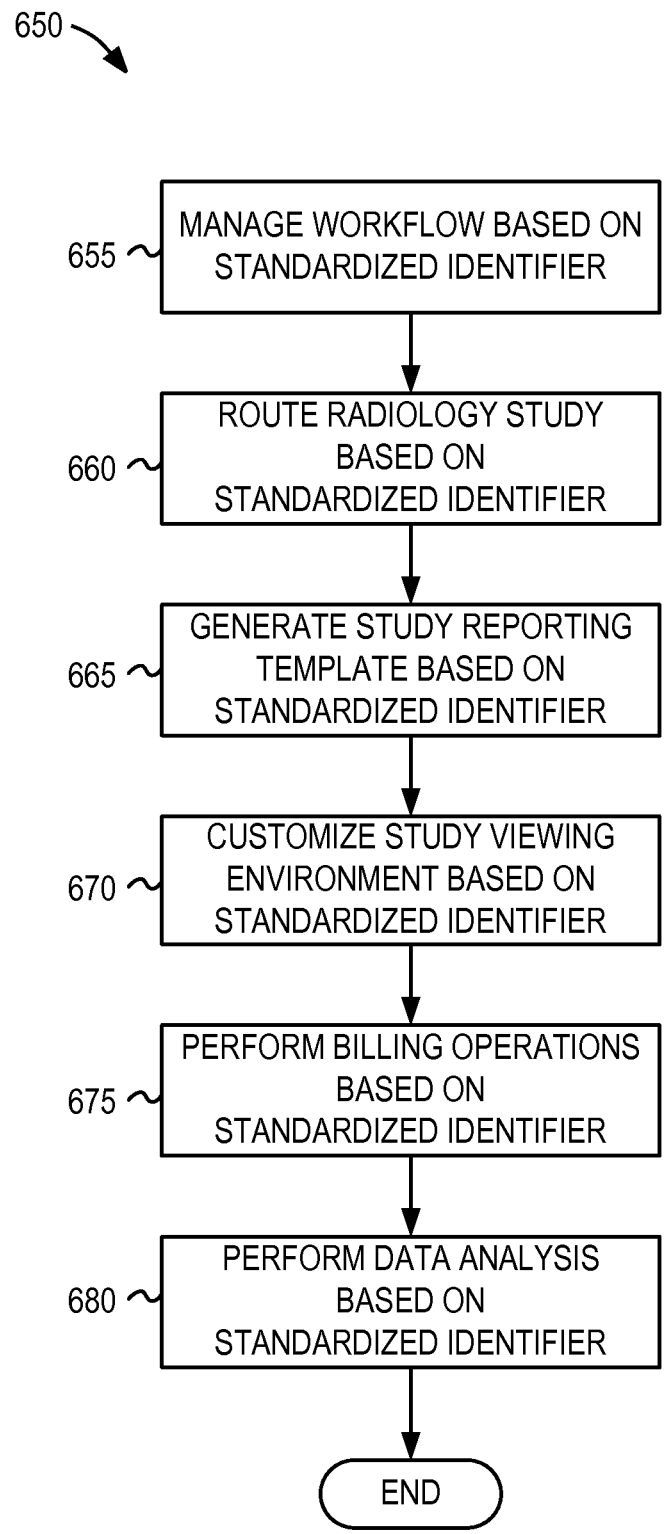
FIG. 6B illustrates a flowchart of additional workflow operations performed with a particular radiology study based on a standardized identifier according to an example described herein.

FIG. 6B provides an illustration of a flowchart 650 of additional workflow operations that may be performed upon a particular radiology study (and associated radiology study data) based on a standardized identifier. The operations depicted in flowchart 650 are provided as example operations, but it will be understood that many of the depicted operations need not occur in sequence, but may occur in parallel, conditionally, or in other variation.

As illustrated, the various operations of flowchart 650 may include client-side and server-side processing operations that are performed with use of the standardized identifier. For example, the operations may include: managing or implementing a workflow for assignment or designation of a radiology study based on the standardized identifier (operation 655), and performing routing of the radiology study based on the standardized identifier (operation 660). For example, the routing may include routing the radiology study to a local radiologist based on an identification and determination from the standardized identifier that the radiology procedure is an interventional radiology procedure. As another example, routing may involve routing the radiology study to a specific remote radiologist involving a subspecialty if the procedure type indicated by the standardized identifier relates to the diagnostic evaluation of the subspecialty.

With the values in the standardized identifier, further operations may be performed at a client viewer or workstation for an assigned radiologist to assist read and diagnostic evaluation. For example, these operations may include generating a custom study reporting template based on the standardized identifier (operation 665), and customizing a study viewing environment based on the standardized identifier (operation 675). The customization to the study reporting template may include adding custom fields for data entry based on the type of radiology study. The customization to the viewing environment may include implementing specific types of hanging protocols or display-implemented features based on the type of the radiology study.

In addition to workflow and routing operations, further analysis and operational management for a medical enterprise may be performed using the standardized identifier. This may include the performance of billing operations (operation 675), or the performance of data analysis (operation 680) in the form of further reports, report analytics, quality assurance, and evaluation activities specific to the radiology procedure type.

Figure 7:
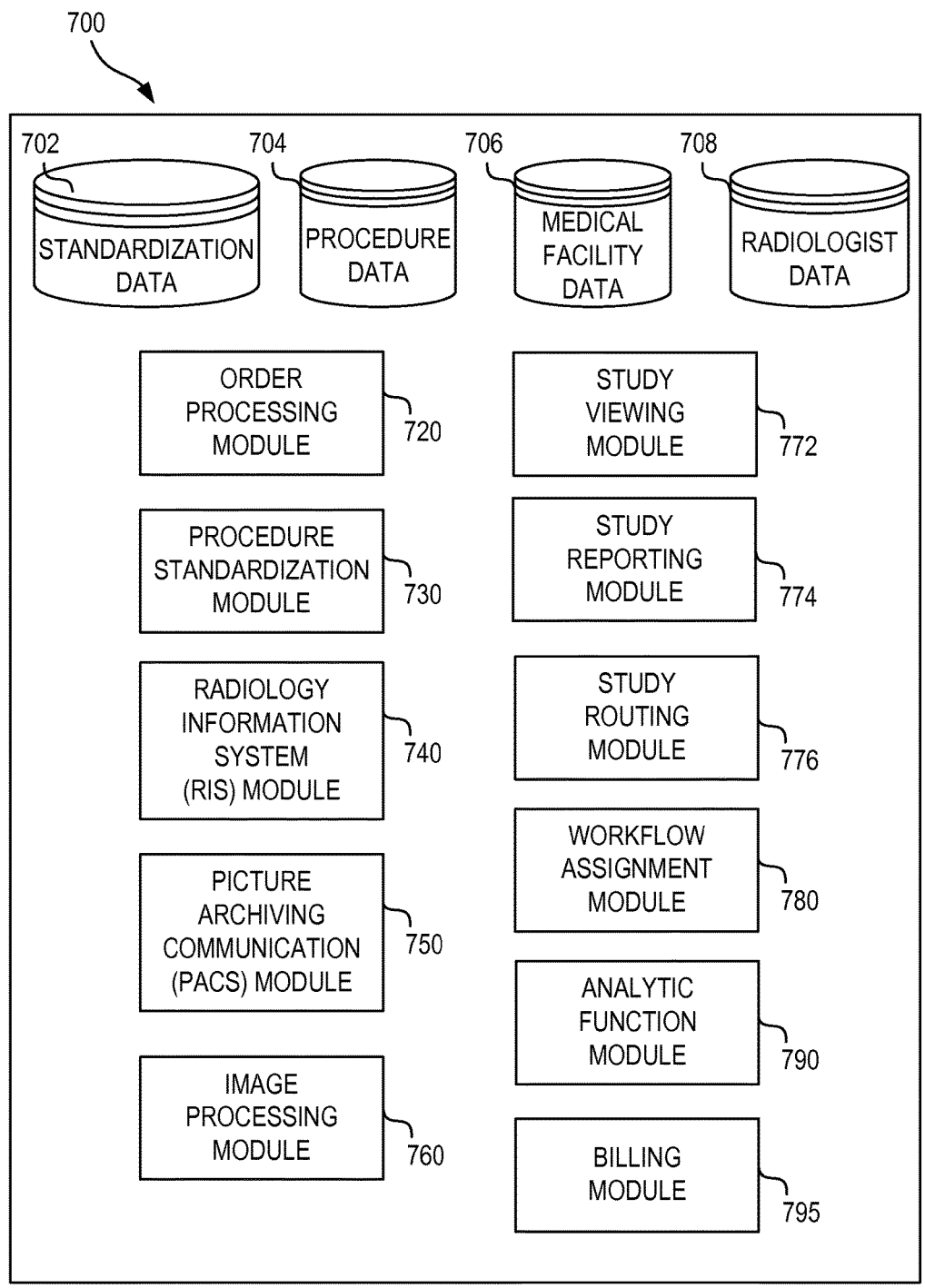
FIG. 7 illustrates a system configuration of a radiology information system arranged to process radiology data according to an example described herein.

FIG. 7 illustrates an example configuration of a system architecture 700 configured to implement the presently described radiology processing system according to an example described herein. System architecture 700 may implement components such as the radiology imaging order processing system 102. The system architecture 700 may include an order processing module 720, a procedure standardization module 730, a radiology information system (RIS) module 740, a picture archiving communication system (PACS) module 750, an image processing module 760, a study viewing module 772, a study reporting module 774, a study routing module 776, a workflow assignment module 780, an analytic function module 790, and a billing module 795. In operation with these modules, the system architecture 700 may further include a plurality of databases or data stores, including a standardization database 702, a procedure database 704, a medical facility database 706, and a radiologist database 708.

The standardization database 702 may provide a location for storage of standardized and normalized data for radiology procedure types. The procedure database 704 may provide a location for storage of information to identify and process respective radiology procedures. The medical facility database 706 may provide a location for storage of information specific to medical facility preferences, requirements, and characteristics related to different radiology procedures. The radiologist database 708 may provide a location for storage of information specific to radiologist preferences, capabilities, and characteristics related to different radiology procedures.

Each of the modules may perform functional operations to effect the radiology procedure standardization techniques described herein. For example, the order processing module 720 may be used to process orders and determine relevant information for radiology procedure types. The procedure standardization module 730 may be used to adapt and conform different radiology procedures into standardized types, and determine which standardized procedure type applies to a particular study. The radiology information module 740 may be used to provide respective information processing functions of a radiology information system (RIS). The picture archiving communication module 750 may be used to provide image storage and access features of a Picture Archiving Communication System (PACS). The image processing module 760 may be used to perform imaging processing operations on imaging data obtained from a respective radiological procedure.

The study viewing module 772 may be used to provide custom study viewing outputs (such as hanging protocols, display characteristics, and the like) based on the characteristics of the imaging study as may be indicated by a standardized identifier. The study reporting module 774 may be used to provide a customized reporting template or fields for the entry of data based on the characteristics of the imaging study as may be indicated by a standardized identifier. The study routing module 776 may be used to route or direct radiology studies among different medical platforms and locations based on the standardized identifier, such as directing a radiology study to be read on-site versus remotely. The workflow assignment module 780 may assign radiology studies to a particular radiologist or set of radiologists, based on qualifications, requirements, preferences, metrics, or other factors. The analytic function module 790 may perform various data analytic activities upon radiology studies and radiology study activities using the characteristics of the standardized radiology procedure types. The billing module 795 may perform various accounting and billing activities according to the characteristics of the standardized radiology procedure types as may be indicated by the standardized identifier.

Although the previous examples were provided with specific reference to radiology imaging procedures and radiology reads, it will be understood that the applicability of the presently described techniques and systems will extend to a variety of medical procedures and specialties, including those not involving traditional radiology imaging modalities. Such specialties include, but are not limited to, pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the use of the normalized identifier and standardized data fields described herein may apply to a variety of medical data types and settings, including medical data with diverging attributes and characteristics.

Figure 8:
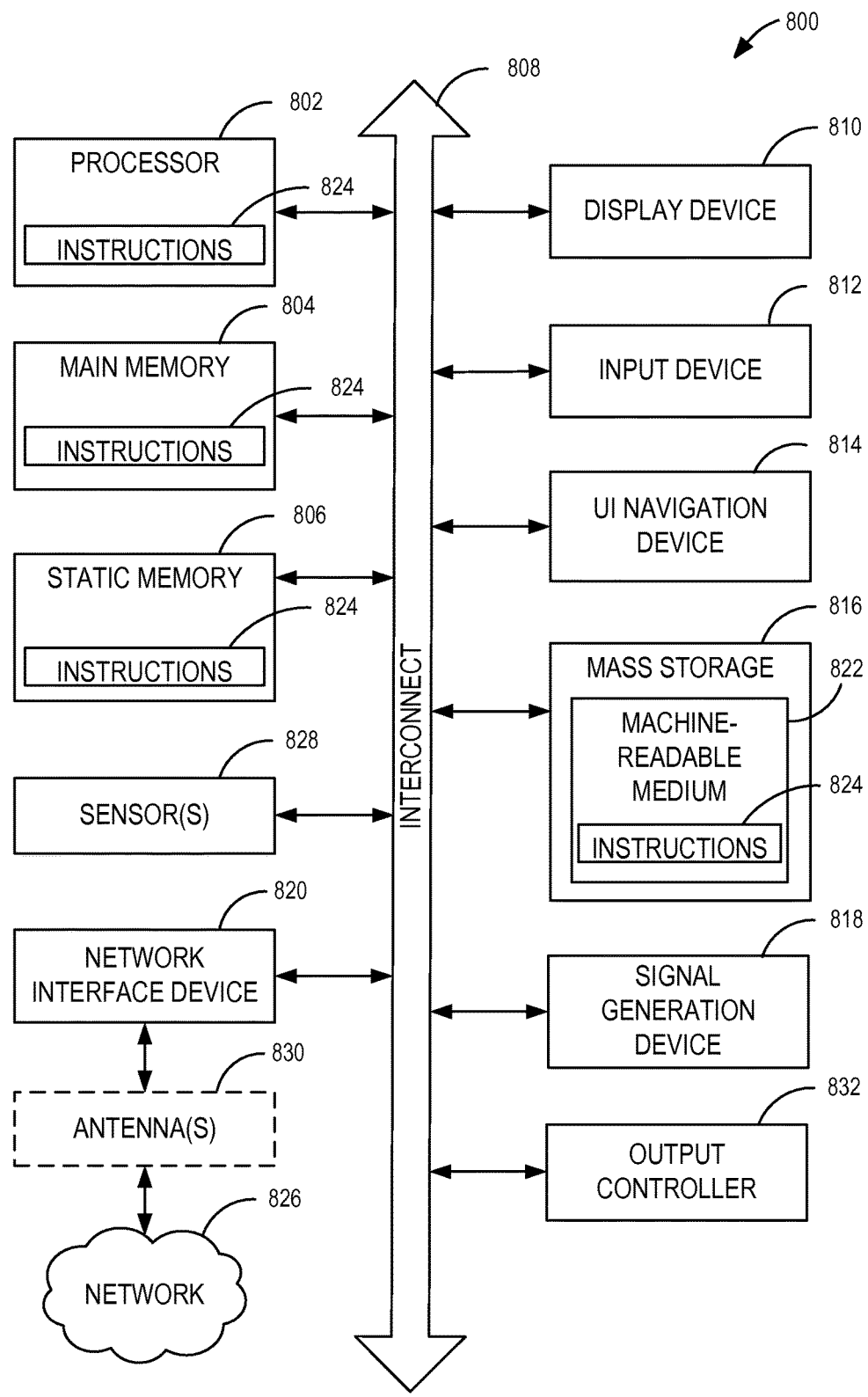
FIG. 8 illustrates an example of a machine configured to perform computing operations according to an example described herein.

FIG. 8 is a block diagram illustrating an example computing system machine 800 upon which any one or more of the methodologies herein discussed may be run according to an example described herein. Computer system 800 may be embodied as a computing device, providing operations of the components featured in the various figures, including components of the radiology imaging order processing system 102, the image review system 106, the imaging system 104, modules and data storage elements in system architecture 700, or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 800 includes a processor 802 (e.g., a central processing unit (CPU), a graphics processing unit (GPU) or both), a main memory 804 and a static memory 806, which communicate with each other via an interconnect 808 (e.g., a link, a bus, etc.). The computer system 800 may further include a video display unit 810, an alphanumeric input device 812 (e.g., a keyboard), and a user interface (UI) navigation device 814 (e.g., a mouse). In one embodiment, the video display unit 810, input device 812 and UI navigation device 814 are a touch screen display. The computer system 800 may additionally include a storage device 816 (e.g., a drive unit), a signal generation device 818 (e.g., a speaker), an output controller 832, and a network interface device 820 (which may include or operably communicate with one or more antennas 830, transceivers, or other wireless communications hardware), and one or more sensors 828.

The storage device 816 includes a machine-readable medium 822 on which is stored one or more sets of data structures and instructions 824 (e.g., software) embodying or utilized by any one or more of the methodologies or functions described herein. The instructions 824 may also reside, completely or at least partially, within the main memory 804, static memory 806, and/or within the processor 802 during execution thereof by the computer system 800, with the main memory 804, static memory 806, and the processor 802 constituting machine-readable media.

While the machine-readable medium 822 is illustrated in an example embodiment to be a single medium, the term "machine-readable medium" may include a single medium or multiple media (e.g., a centralized or distributed database, and/or associated caches and servers) that store the one or more instructions 824. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the modules in the system architecture 700 of the radiology processing system may be client-operated software or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Additional examples of the presently described method, system, and device embodiments are suggested according to the structures and techniques described herein. Other non-limiting examples may be configured to operate separately, or can be combined in any permutation or combination with any one or more of the other examples provided above or throughout the present disclosure.

Example 1 includes the subject matter embodied by a method performed by a computing device with at least one processor and memory, with the method implemented by operations performed using the processor and the memory, the operations comprising: processing data associated with a particular medical imaging procedure to obtain characteristics of the particular medical imaging procedure; identifying multiple standardized data values using the characteristics of the particular medical imaging procedure, wherein the identified multiple standardized data values are selected respectively from among available values of standardized data fields; and assigning a normalized procedure identifier to the data associated with the particular medical imaging procedure, the normalized procedure identifier including the multiple standardized data values, wherein the normalized procedure identifier is used for identification of a particular type of medical imaging procedure.

In Example 2, the subject matter of Example 1 can optionally include the available values of the standardized data values reflecting identifiable characteristics of multiple types of medical imaging procedures; wherein the particular type of medical imaging procedure is identified among the multiple types of medical imaging procedures; and wherein the normalized procedure identifier is further designated for assignment to a plurality of medical imaging procedures originating from among multiple medical facilities for the particular type of medical imaging procedure.

In Example 3, the subject matter of one or any combination of Examples 1-2 can optionally include routing the data associated with the particular medical imaging procedure for a diagnostic evaluation of images produced from the particular medical imaging procedure, the routing performed for the particular type of medical imaging procedure based on use of the normalized procedure identifier.

In Example 4, the subject matter of one or any combination of Examples 1-3 can optionally include the particular medical imaging procedure being a radiological imaging procedure, wherein the data associated with the particular medical imaging procedure includes radiology procedure data produced for a radiology study, wherein the radiology procedure data includes order data of an radiology read request and image data of images produced by an imaging modality, with the operations of the method further comprising: identifying a first portion of the data associated with the particular medical imaging procedure from the order data from the radiology read request; and identifying a second portion of the data associated with the particular medical imaging procedure from the image data produced by the imaging modality; wherein assigning a normalized procedure identifier to the data associated with the particular medical imaging procedure is performed based on an identification of the particular type of medical imaging procedure from a plurality of defined radiological study types, using the first portion of the data and the second portion of the data associated with the particular medical imaging procedure.

In Example 5, the subject matter of one or any combination of Examples 1-4 can optionally include the normalized procedure identifier including a human-readable representation, wherein portions of the normalized procedure identifier represent the identified multiple standardized data values with respective alphanumeric values, wherein the identified multiple standardized data fields include fields for the particular type of medical imaging procedure that designate: an imaging modality type, a use of contrast, and a body region.

In Example 6, the subject matter of one or any combination of Examples 1-5 can optionally include the multiple standardized data fields further including a field for the particular type of medical imaging procedure that designate: a remote or local interpretation, and a procedure code.

In Example 7, the subject matter of one or any combination of Examples 1-6 can optionally include the normalized procedure identifier being constructed from standardized data values associated with standardized data characteristics, the standardized data characteristics including at least one of: a CPT (Current Procedural Terminology) description; a CPT (Current Procedural Terminology) code; an imaging modality designation; a functional modality designation; a CMS (Centers for Medicare & Medicaid) RVU (relative value unit) value; a contrast usage designation; a body region value; an intravenous line (IV) designation; a radiologist location designation; a primary subspecialty designation; a secondary subspecialty designation; an internal procedure code; or an internal procedure description.

In Example 8, the subject matter of one or any combination of Examples 1-7 can optionally include wherein the particular medical imaging procedure is a radiology imaging procedure, the operations of the method further comprising: using the normalized procedure identifier to generate a radiology analytics report, wherein the radiology analytics report includes information for processing activities of radiology studies within a medical enterprise for the particular type of medical imaging procedure, wherein the processing activities of radiology studies within the medical enterprise are identified with use of the normalized procedure identifier.

In Example 9, the subject matter of one or any combination of Examples 1-8 can optionally include performing data analysis on data associated with respective procedures of multiple medical imaging procedures, the multiple medical imaging procedures including the particular medical imaging procedure, wherein the respective procedures are identified with use of the normalized procedure identifier.

Example 10 can include, or can optionally be combined with all or portions of the subject matter of one or any combination of Examples 1-9 to include the subject matter embodied by a non-transitory machine-readable medium, the machine-readable medium including instructions, which when executed by a machine having at least one hardware processor, causes the machine to perform operations including: processing an instance of data produced from a medical imaging procedure to determine characteristics of the medical imaging procedure; identifying multiple standardized data values from multiple standardized data fields defined for various medical imaging procedures, the multiple standardized data values being identified from the determined characteristics of the medical imaging procedure; and assigning a standardized procedure identifier to a type of the medical imaging procedure, the standardized procedure identifier constructed from the multiple standardized data values identified from the determined characteristics of the medical imaging procedure.

In Example 11, the subject matter of Example 10 can optionally include routing the instance of data produced from the medical imaging procedure, the routing being performed to facilitate a diagnostic evaluation of the type of the medical imaging procedure, and the routing being performed using the standardized procedure identifier.

In Example 12, the subject matter of one or any combination of Examples 10-11 can optionally include the instance of data produced from the medical imaging procedure providing radiology procedure data, and wherein the medical imaging procedure is a radiological imaging procedure, the instructions further operable to cause the machine to perform operations including: processing the radiology procedure data, the radiology procedure data originating from a medical facility conducting the radiological imaging procedure; identifying a first portion of the standardized data values from an order produced with the radiological imaging procedure; and identifying a second portion of the standardized data values from a set of medical images produced with the radiological imaging procedure; wherein identifying the multiple standardized data values from multiple standardized data fields defined for various medical imaging procedures includes identifying the determined characteristics of the radiological imaging procedure occurring at the medical facility, using the first portion and the second portion of the standardized data values.

In Example 13, the subject matter of one or any combination of Examples 10-12 can optionally include the multiple standardized data fields providing data values respectively for designating: an imaging modality type used in the medical imaging procedure, a use of contrast in the medical imaging procedure, and a body region designated with the medical imaging procedure.

In Example 14, the subject matter of one or any combination of Examples 10-13 can optionally include the standardized procedure identifier being embodied by a human-readable representation having portions of the standardized procedure identifier representing respective values of the data values for the multiple standardized data fields, the data values for the multiple standardized data fields for the medical imaging procedure designating: use of an imaging modality type in the medical imaging procedure, use of contrast in the medical imaging procedure, and a body region designated in the medical imaging procedure.

In Example 15, the subject matter of one or any combination of Examples 10-14 can optionally include the standardized procedure identifier being correlated to multiple standardized data characteristics, the multiple standardized data characteristics including at least one of: a CPT (Current Procedural Terminology) description; a CPT (Current Procedural Terminology) code; an imaging modality designation; a functional modality designation; a CMS (Centers for Medicare & Medicaid) RVU (relative value unit) value; a contrast usage designation; a body region value; an intravenous line (IV) designation; a radiologist location designation; a primary subspecialty designation; a secondary subspecialty designation; an internal procedure code; or an internal procedure description.

Example 16 can include, or can optionally be combined with all or portions of the subject matter of one or any combination of Examples 1-15 to include the subject matter embodied by a system (e.g., an information system), comprising: at least one processor and memory; a procedure standardization module implemented in connection with instructions executing with use of the processor and memory, the instructions configured to: process an instance of imaging data produced from a medical imaging procedure of a particular type of medical imaging procedure; identify multiple data values from the instance of imaging data, the multiple data values identified from a combination of standardized data values established respectively for a multiple standardized data fields; and assign a standardized identifier to identify the particular type of the medical imaging procedure, the standardized identifier corresponding to the combination of standardized data values established for the multiple standardized data fields.

In Example 17, the subject matter of Example 16 can optionally include the medical imaging procedure producing data for a radiology study, and the system further comprising a radiology information system (RIS) module, the RIS module configured to correlate the radiology study in a RIS instance with the particular type of the medical imaging procedure based on use of the standardized identifier.

In Example 18, the subject matter of one or any combination of Examples 16-17 can optionally include the medical imaging procedure producing data for a radiology study, and the system further comprising a Picture Archiving Communication System (PACS) module, the PACS module configured to receive and process images produced from the particular type of the medical imaging procedure in a PACS instance based on use of the standardized identifier.

In Example 19, the subject matter of one or any combination of Examples 16-18 can optionally include an image processing module configured to perform image processing on an image set associated with the medical imaging procedure, the image processing module configured to obtain values for the standardized identifier as a result of accessing the image set and extracting metadata from the image set, the metadata including patient information or medical facility information; and an order processing module configured to perform order processing operations with an order associated with the medical imaging procedure, the order processing operations including determining whether the image set is to be forwarded to an image review system, and correlating the image set with a radiology order based on the standardized identifier.

In Example 20, the subject matter of one or any combination of Examples 16-19 can optionally include a workflow assignment module, the workflow assignment module configured to implement a workflow for an assignment of the imaging data based on workflow criteria, the workflow criteria including at least one of: radiologist qualifications, radiologist requirements, radiologist preferences, or radiologist metrics.

In Example 21, the subject matter of one or any combination of Examples 16-20 can optionally include the standardized identifier being a normalized procedure identifier, the system further comprising a procedure standardization module configured to implement a use of the normalized procedure identifier in a medical information system, by performing operations including: establishing a mapping between a plurality of medical imaging procedure types and a normalized procedure type, wherein the normalized procedure type is correlated to an additional identifier; designating a normalized procedure identifier for the normalized procedure type; and assigning the normalized procedure identifier to data associated with a particular medical imaging procedure, based on a plurality of data values from the particular medical imaging procedure that correspond to standardized values for a plurality of standardized data fields; and processing data from the particular medical imaging procedure based on use of the normalized procedure identifier, wherein the normalized procedure identifier is mapped to a plurality of standardized characteristics.

In Example 22, the subject matter of one or any combination of Examples 16-21 can optionally include an analytics function module, the analytics function module configured to process a plurality of standardized identifiers to generate a radiology analytics report for radiology studies, wherein the radiology analytics report includes information for processing activities of radiology studies within a medical enterprise, the processing activities including operations for how radiology studies are retrieved, analyzed, enhanced, and exchanged throughout a medical enterprise.

Example 23 can include, or can optionally be combined with all or portions of the subject matter of one or any combination of Examples 1-22 to include the subject matter embodied by a method, performed by a computing device having at least one processor and memory, the method implemented by operations performed using the processor and the memory, with the operations comprising: establishing a mapping between a plurality of medical imaging procedure types and a normalized procedure type; designating a normalized procedure identifier for the normalized procedure type; assigning the normalized procedure identifier to data associated with a particular medical imaging procedure, based on a plurality of data values for the particular medical imaging procedure that correspond to standardized data values for standardized data fields of characteristics for medical imaging procedures; and processing data from the particular medical imaging procedure based on use of the normalized procedure identifier, wherein the normalized procedure identifier identifies characteristics for the particular medical imaging procedure that are in common with other medical imaging procedures of the normalized procedure type.

In Example 24, the subject matter of Example 23 can optionally include routing the data from the particular medical imaging procedure to a particular destination based on the normalized procedure identifier, the particular destination based on a match with one or more of the characteristics for the particular medical imaging procedure.

In Example 25, the subject matter of one or any combination of Examples 23-24 can optionally include the particular medical imaging procedure being a radiological imaging study, the radiological imaging study associated with a radiology order stored in an information system and radiology imaging data stored in an imaging system.

In Example 26, the subject matter of one or any combination of Examples 23-25 can optionally include the normalized procedure identifier including: a modality indication, a contrast indication, and a body region indication.

In Example 27, the subject matter of one or any combination of Examples 23-26 can optionally include the modality indication being provided from a value indicating: Computed Tomography Angiography, Computed Tomography, Interventional Radiology, Fluoroscope, Magnetic Resonance Angiography, Magnetic Resonance, Nuclear Medicine, Positron Emission Tomography, Ultrasound, or X-Ray; the contrast indication is provided from an alphanumeric value indicating: with contrast, without contrast, or with and without contrast; the body region indication is provided from an alphanumeric value indicating: Abdomen, Breast, Chest, Head, Neck, Lower Extremity, Pelvis, General, Spine, Upper Extremity, or Whole Body.

In Example 28, the subject matter of one or any combination of Examples 23-27 can optionally include the normalized procedure identifier further including: a remote or local indication, and a unique procedure indication; wherein the remote or local indication is provided from an alphanumeric value indicating a local or remote procedure, and wherein the unique procedure indication is provided from an alphanumeric value indicating the normalized procedure type.

The following claims are hereby incorporated into the detailed description, with each claim standing on its own as a separate embodiment.

What is claimed is:

1. A method, performed by a computing device with at least one processor and memory, the method implemented by operations performed using the processor and the memory, with the operations comprising:
    processing data associated with a particular medical imaging procedure to obtain characteristics of the particular medical imaging procedure, wherein the data associated with the particular medical imaging procedure includes a source medical imaging procedure identifier applied by a source medical facility;
    identifying multiple standardized data values using the characteristics of the particular medical imaging procedure, wherein the identified multiple standardized data values are selected respectively from among available values of multiple standardized data fields;
    assigning a normalized procedure identifier to the data associated with the particular medical imaging procedure, the normalized procedure identifier providing a pre-defined value that represents a combination of the multiple standardized data values, wherein the normalized procedure identifier provides identification of a particular type of medical imaging procedure, and wherein the normalized procedure identifier is associated with the source medical imaging procedure identifier that is applied by the source medical facility to identify the particular type of medical imaging procedure; and
    recording, in a medical information system, the assigning of the normalized procedure identifier to the data associated with the particular medical imaging procedure;
    wherein the normalized procedure identifier is associated with additional medical procedure identifiers that are respectively applied by other medical facilities to identify the particular type of medical imaging procedure.

2. The method of claim 1, wherein the available values of the standardized data values reflect identifiable characteristics of multiple types of medical imaging procedures, and wherein the particular type of medical imaging procedure is identified among the multiple types of medical imaging procedures.

3. The method of claim 1, the operations of the method further comprising:
    routing the data associated with the particular medical imaging procedure for a diagnostic evaluation of images produced from the particular medical imaging procedure, the routing performed for the particular type of medical imaging procedure based on use of the normalized procedure identifier.

4. The method of claim 1, wherein the particular medical imaging procedure is a radiological imaging procedure, wherein the data associated with the particular medical imaging procedure includes radiology procedure data produced for a radiology study, wherein the radiology procedure data includes order data of an radiology read request and image data of images produced by an imaging modality, with the operations of the method further comprising:
    identifying a first portion of the data associated with the particular medical imaging procedure from the order data of the radiology read request; and
    identifying a second portion of the data associated with the particular medical imaging procedure from the image data produced by the imaging modality;
    wherein assigning the normalized procedure identifier to the data associated with the particular medical imaging procedure is performed based on an identification of the particular type of medical imaging procedure from a plurality of defined radiological study types, using the first portion of the data and the second portion of the data associated with the particular medical imaging procedure.

5. The method of claim 1, wherein the normalized procedure identifier includes a human-readable representation, wherein portions of the normalized procedure identifier represent the identified multiple standardized data values with respective alphanumeric values, wherein the human-readable representation of the normalized procedure identifier is provided from a concatenation of the respective alphanumeric values, and wherein the multiple standardized data fields include fields for the particular type of medical imaging procedure that designate: an imaging modality type, a use of contrast, and a body region.

6. The method of claim 5, wherein the standardized data fields further include a field for the particular type of medical imaging procedure that designate: a remote or local interpretation, and a procedure code.

7. The method of claim 1, wherein the normalized procedure identifier is constructed from standardized data values associated with standardized data characteristics, the standardized data characteristics including at least one of:
a CPT (Current Procedural Terminology) description;
a CPT (Current Procedural Terminology) code;
an imaging modality designation;
a functional modality designation;
a CMS (Centers for Medicare & Medicaid) RVU (relative value unit) value;
a contrast usage designation;
a body region value;
an intravenous line (IV) designation;
a radiologist location designation;
a primary subspecialty designation;
a secondary subspecialty designation;
an internal procedure code;
or an internal procedure description.

8. The method of claim 1, wherein the particular medical imaging procedure is a radiology imaging procedure, the operations of the method further comprising:
generating a radiology analytics report based on use of the normalized procedure identifier, wherein the radiology analytics report includes information for processing activities of radiology studies within a medical enterprise for the particular type of medical imaging procedure, wherein the processing activities of radiology studies within the medical enterprise are identified with use of the normalized procedure identifier.

9. The method of claim 1, the operations of the method further comprising:
performing data analysis on data associated with respective procedures of multiple medical imaging procedures, the multiple medical imaging procedures including the particular medical imaging procedure, wherein the respective procedures are identified with use of the normalized procedure identifier.

10. A non-transitory machine-readable medium, the machine-readable medium including instructions, which when executed by a machine having at least one hardware processor, causes the machine to perform operations including:
processing an instance of data produced from a medical imaging procedure to determine characteristics of the medical imaging procedure, wherein the data produced from the medical imaging procedure includes a source medical imaging procedure identifier used by a source medical facility;
identifying multiple standardized data values from multiple standardized data fields defined for various characteristics of medical imaging procedures, the multiple standardized data values being identified from the determined characteristics of the medical imaging procedure;
assigning a standardized procedure identifier to a type of the medical imaging procedure, wherein the standardized procedure identifier is a pre-defined value that is constructed from a combination of the multiple standardized data values identified from the determined characteristics of the medical imaging procedure, wherein the standardized procedure identifier is associated with the source medical imaging procedure identifier that is used by the source medical facility to identify the type of the medical imaging procedure; and
recording, in a medical information system, the assigning of the standardized procedure identifier to the data associated with the medical imaging procedure;
wherein the standardized procedure identifier is associated with additional medical procedure identifiers used respectively among other medical facilities to identify the type of the medical imaging procedure.

11. The machine-readable medium of claim 10, the instructions further executed to cause the machine to perform operations including routing the instance of data produced from the medical imaging procedure, the routing being performed to facilitate a diagnostic evaluation of the type of the medical imaging procedure, and the routing being performed using the standardized procedure identifier.

12. The machine-readable medium of claim 10, wherein the instance of data produced from the medical imaging procedure provides radiology procedure data, and wherein the medical imaging procedure is a radiological imaging procedure, the instructions further executed to cause the machine to perform operations including:
processing the radiology procedure data, the radiology procedure data originating from a medical facility conducting the radiological imaging procedure;
identifying a first portion of the standardized data values from an order produced with the radiological imaging procedure; and
identifying a second portion of the standardized data values from a set of medical images produced with the radiological imaging procedure; wherein identifying the multiple standardized data values from multiple standardized data fields defined for various medical imaging procedures includes identifying the determined characteristics of the radiological imaging procedure occurring at the medical facility, using the first portion and the second portion of the standardized data values.

13. The machine-readable medium of claim 10, wherein the multiple standardized data fields provide data values respectively for designating: an imaging modality type used in the medical imaging procedure, a use of contrast in the medical imaging procedure, and a body region designated with the medical imaging procedure.

14. The machine-readable medium of claim 10, wherein the standardized procedure identifier is embodied by a human-readable representation having portions of the standardized procedure identifier representing respective values of the data values for the multiple standardized data fields, the data values for the multiple standardized data fields for the medical imaging procedure designating: use of an imaging modality type in the medical imaging procedure, use of contrast in the medical imaging procedure, and a body region designated in the medical imaging procedure.

15. The machine-readable medium of claim 10, wherein the standardized procedure identifier is correlated to multiple standardized data characteristics, the multiple standardized data characteristics including at least one of:
a CPT (Current Procedural Terminology) description;
a CPT (Current Procedural Terminology) code;
an imaging modality designation;
a functional modality designation;
a CMS (Centers for Medicare & Medicaid) RVU (relative value unit) value;
a contrast usage designation;
a body region value;
an intravenous line (IV) designation;

a radiologist location designation;
a primary subspecialty designation;
a secondary subspecialty designation;
an internal procedure code; or
an internal procedure description.

16. A system, comprising:
    at least one processor and memory;
    a procedure standardization module implemented with instructions executing via the processor and memory, the instructions configured to:
        process an instance of imaging data produced from a medical imaging procedure of a particular type of medical imaging procedure, wherein the imaging data produced from the medical imaging procedure includes a source medical imaging procedure identifier applied by a source medical facility;
        identify multiple data values from the instance of imaging data, the multiple data values identified from a combination of standardized data values established respectively for multiple standardized data fields;
        assign a standardized identifier to identify the particular type of the medical imaging procedure, wherein the standardized identifier is a pre-defined value that is constructed from the combination of standardized data values established for the multiple standardized data fields, wherein the standardized identifier is associated with the source medical imaging procedure identifier that is used by the source medical facility to identify the particular type of the medical imaging procedure;
        record, in a medical information system, assignment of the standardized identifier to the data associated with the medical imaging procedure;
        wherein the standardized identifier is associated with additional medical procedure identifiers that are respectively applied by other medical facilities to identify the particular type of the medical imaging procedure.

17. The system of claim 16, wherein the medical imaging procedure produces data for a radiology study, and the system further comprising a radiology information system (RIS) module implemented with instructions executing via the processor and memory, the RIS module configured to correlate the radiology study in a RIS instance with the particular type of the medical imaging procedure based on use of the standardized identifier.

18. The system of claim 16, wherein the medical imaging procedure produces data for a radiology study, and the system further comprising a Picture Archiving Communication System (PACS) module implemented with instructions executing via the processor and memory, the PACS module configured to receive and process images produced from the particular type of the medical imaging procedure in a PACS instance based on use of the standardized identifier.

19. The system of claim 16, the system further comprising:
    an image processing module implemented with instructions executing via the processor and memory, the image processing module configured to perform image processing on an image set associated with the medical imaging procedure, the image processing module configured to obtain values for the standardized identifier as a result of accessing the image set and extracting metadata from the image set, the metadata including patient information or medical facility information; and
    an order processing module implemented with instructions executing via the processor and memory, the order processing module configured to perform order processing operations with an order associated with the medical imaging procedure, the order processing operations including determining whether the image set is to be forwarded to an image review system, and correlating the image set with a radiology order based on the standardized identifier.

20. The system of claim 16, the system further comprising a workflow assignment module implemented with instructions executing via the processor and memory, the workflow assignment module configured to implement a workflow for an assignment of the imaging data based on workflow criteria, the workflow criteria including at least one of:
    radiologist qualifications, radiologist requirements, radiologist preferences, or radiologist metrics.

21. The system of claim 16, wherein the standardized identifier is a normalized procedure identifier, wherein the procedure standardization module is further configured to implement a use of the normalized procedure identifier in the medical information system, by performing operations including:
    establishing a mapping between a plurality of medical imaging procedure types and a normalized procedure type, wherein the normalized procedure type is correlated to an additional identifier;
    designating the normalized procedure identifier for the normalized procedure type;
    assigning the normalized procedure identifier to data associated with a particular medical imaging procedure, based on a plurality of data values from the particular medical imaging procedure that correspond to standardized values for a plurality of standardized data fields; and
    processing data from the particular medical imaging procedure based on use of the normalized procedure identifier, wherein the normalized procedure identifier is mapped to a plurality of standardized characteristics.

22. The system of claim 16, further comprising an analytics function module implemented with instructions executing via the processor and memory, the analytics function module configured to process a plurality of standardized identifiers to generate a radiology analytics report for radiology studies, wherein the radiology analytics report includes information for processing activities of radiology studies within a medical enterprise, the processing activities including operations for how radiology studies are retrieved, analyzed, enhanced, and exchanged throughout the medical enterprise.

23. A method, performed by a computing device having at least one processor and memory, the method implemented by operations performed using the processor and the memory, with the operations comprising:
    establishing a mapping between a plurality of medical imaging procedure types and a normalized procedure type;
    designating a normalized procedure identifier for the normalized procedure type, wherein the normalized procedure identifier is associated with distinct medical procedure identifiers applied by respective medical facilities to identify the plurality of medical imaging procedure types;
    assigning the normalized procedure identifier to data associated with a particular medical imaging procedure, based on a plurality of data values for the particular medical imaging procedure that correspond to standardized data values for standardized data fields of characteristics for medical imaging procedures, wherein the data associated with the particular medical imaging procedure includes a source procedure identifier used by a source medical facility, wherein the source procedure identifier is one of the distinct procedure medical identifiers, and wherein the normalized procedure identifier is a pre-defined value that represents a combination of the standardized data values; and processing data from the particular medical imaging procedure based on use of the normalized procedure identifier, wherein the normalized procedure identifier identifies characteristics for the particular medical imaging procedure that are in common with other medical imaging procedures of the normalized procedure type.

24. The method of claim 23, further comprising:
routing the data from the particular medical imaging procedure to a particular destination based on the normalized procedure identifier, the particular destination based on a match with one or more of the characteristics for the particular medical imaging procedure.

25. The method of claim 24, wherein the particular medical imaging procedure is a radiological imaging study, the radiological imaging study associated with a radiology order stored in an information system and radiology imaging data stored in an imaging system.

26. The method of claim 23, wherein the normalized procedure identifier includes: a modality indication, a contrast indication, and a body region indication.

27. The method of claim 26, wherein:
the modality indication is provided from a value indicating: Computed Tomography Angiography, Computed Tomography, Interventional Radiology, Fluoroscope, Magnetic Resonance Angiography, Magnetic Resonance, Nuclear Medicine, Positron Emission Tomography, Ultrasound, or X-Ray;
the contrast indication is provided from an alphanumeric value indicating: with contrast, without contrast, or with and without contrast; and
the body region indication is provided from an alphanumeric value indicating: Abdomen, Breast, Chest, Head, Neck, Lower Extremity, Pelvis, General, Spine, Upper Extremity, or Whole Body.

28. The method of claim 27, wherein the normalized procedure identifier further includes:
a remote or local indication, and a unique procedure indication;
wherein the remote or local indication is provided from an alphanumeric value indicating a local or remote procedure, and wherein the unique procedure indication is provided from an alphanumeric value indicating the normalized procedure type.

\* \* \* \* \*